(12) United States Patent
Purcell et al.

(10) Patent No.: US 9,414,706 B2
(45) Date of Patent: Aug. 16, 2016

(54) GLOVE DISPENSING APPARATUS AND GLOVE CARTRIDGE FOR USE THEREWITH AND GLOVE DISPENSING METHOD

(76) Inventors: David Scott Purcell, Changler, AZ (US); John Robert Morris, Chandler, AZ (US)

(*) Notice: Subject to any disclaimer, the term of this patent is extended or adjusted under 35 U.S.C. 154(b) by 263 days.

(21) Appl. No.: 14/114,658

(22) PCT Filed: Apr. 27, 2012

(86) PCT No.: PCT/US2012/035451
§ 371 (c)(1),
(2), (4) Date: Jun. 26, 2014

(87) PCT Pub. No.: WO2012/149315
PCT Pub. Date: Nov. 1, 2012

(65) Prior Publication Data
US 2014/0305974 A1   Oct. 16, 2014

Related U.S. Application Data

(60) Provisional application No. 61/481,005, filed on Apr. 29, 2011.

(51) Int. Cl.
*A47G 25/90* (2006.01)

(52) U.S. Cl.
CPC .................... *A47G 25/904* (2013.01)

(58) Field of Classification Search
CPC ................................................ A47G 25/904
See application file for complete search history.

(56) References Cited

U.S. PATENT DOCUMENTS

| | | |
|---|---|---|
| 3,695,463 A | 10/1972 | Weisker et al. |
| 4,002,276 A | 1/1977 | Poncy et al. |
| 4,155,494 A | 5/1979 | Poncy et al. |
| 4,889,266 A | 12/1989 | Wight |
| 4,915,272 A | 4/1990 | Vlock |
| 5,058,785 A | 10/1991 | Rich et al. |
| 5,078,308 A | 1/1992 | Sullivan |
| 5,868,290 A | 2/1999 | Green, Sr. et al. |
| 6,053,380 A | 4/2000 | Sherrod |
| 6,435,888 B1 | 8/2002 | Reed, Jr. |
| 6,832,708 B2 | 12/2004 | Sinai |
| 6,932,253 B2 | 8/2005 | Sato |
| 7,377,410 B1 | 5/2008 | Webb |
| 8,651,323 B2* | 2/2014 | Balkin ............... A47K 10/32  2/159 |
| 2014/0305974 A1* | 10/2014 | Purcell ............... A47G 25/904  223/111 |

OTHER PUBLICATIONS

International Search Report (PCT/ISA/210) dated Jul. 6, 2012 (one (1) page).
International Preliminary Report Dated Nov. 7, 2013 (Five (5) pages).

\* cited by examiner

*Primary Examiner* — Shaun R Hurley
*Assistant Examiner* — Andrew W Sutton
(74) *Attorney, Agent, or Firm* — Crowell & Moring LLP

(57) ABSTRACT

An apparatus for dispensing a disposable glove and applying it to the hand of a user. A stream of air drawn into an enclosed glove applying chamber through a constricted opening aligned with the heel of the glove inflates the topmost glove in a stack of gloves in the chamber so that a user can readily insert his hand into the glove. After the user has donned the glove on the hand, a wall of the chamber is opened to permit the user to readily withdraw his hand from the glove applying chamber while the air flow which originally inflated the topmost glove is disrupted. Upon closure of the chamber wall, the re-established air flow automatically inflates the next lower glove in the glove stack to prepare the next glove for receipt of another hand.

20 Claims, 5 Drawing Sheets

GLOVE DISPENSING APPARATUS AND GLOVE CARTRIDGE FOR USE THEREWITH AND GLOVE DISPENSING METHOD

This application is a National Phase of PCT International Application No. PCT/US12/35451, filed Apr. 27, 2012, which claims priority from U.S. Provisional Patent Application Ser. No. 61/481,005, filed Apr. 29, 2011, the entire disclosures of which are herein expressly incorporated by reference.

BACKGROUND OF THE INVENTION

In food service and food handling industries, public health considerations have lead to rules mandating that workers wear gloves when handling food. Corresponding requirements also exist in other industries. In sandwich shops and similar establishments where workers successively serve a series of customers, it may be required in order to prevent cross-contamination that the workers don a new set of gloves for each customer. As a result, there is a need for inexpensive gloves which are readily disposable. Such gloves are commonly made from two layers of polymeric film cut to the general shape of a hand and heat sealed around the periphery to form an enclosure for the hand.

In many cases, however, such gloves can be difficult to apply. The thin polymeric films from which the gloves are made can be difficult to grip. Static charges or natural adhesion may cause the layers to adhere to each other, thereby making it difficult for a user to open the glove for insertion of the hand. Service delays which occur as workers struggle to put on a new set of disposable gloves reduce the overall efficiency of food service establishments. It would be highly desirable for such businesses if an apparatus were available to facilitate rapid and reliable donning of a new disposable glove by the personnel of the establishment.

Efforts have been made in the past to devise glove applying devices, particularly for surgical gloves. Such devices, however, have tended to be complicated and/or to involve complex structural arrangements, such as tight peripheral seals, unsuited to the dispensing of lightweight and inexpensive food service gloves. For example, U.S. Pat. No. 3,695,463 discloses a system in which an individual glove is inserted into a vacuum-generating machine, where each individual glove must be first handled and a seal between the wrist opening of the glove and the vacuum-generating machine must be created. The need to individually handle the gloves and to positively seal the wrist region of the glove to permit a strong vacuum to be generated (such as by clamping the wrist region of the glove on the vacuum-generating machine, rolling the wrist region over a rim of the vacuum-generating machine, or providing a rigid ring about the glove wrist area to support the glove when located in the vacuum-generating machine) is a problem common to a number of such designs, for example, as disclosed in U.S. Pat. Nos. 4,002,276, 4,155,494, 4,889,266, 4,915,272, 5,058,785, 5,078,308, 5,868,290, 6,053,380, 6435,388, 6,832,708 and 6,932,253.

SUMMARY OF THE INVENTION

It is therefore an object of the invention to provide an improved apparatus for dispensing and applying a glove to the hand of a user.

Another object of the invention is to provide an apparatus for dispensing and applying a glove to the hand of a user which is structurally uncomplicated, yet reliable and can be produced at reasonable cost.

A further object of the invention is to provide an apparatus for dispensing and applying a glove to the hand of a user which avoids the need for the user to fumble with the glove and facilitates rapid and convenient application of a glove.

An additional object of the invention is to provide an apparatus for dispensing and applying a glove to the hand of a user which can be used repeatedly in rapid succession.

It is also an object of the invention to provide as an article of manufacture a glove cartridge or stack of gloves adapted to be dispensed and applied to the hand of a user by the aforedescribed glove dispensing and applying apparatus.

Another object of the invention is to provide an apparatus which does not rely on a completely sealed container in order to enable the opening of a glove to permit insertion of a hand.

A further object of the invention is to provide a method for donning a glove in which individual gloves are inflated by the use of gas flow around the glove so as to present the open heel of the glove (i.e., the glove wrist opening) to a user for donning, without the need for sealed containers or pre-mounting of the glove on a glove-holding apparatus.

These and other objects of the invention have been achieved by providing a glove opening and dispensing machine in which air flow is developed over a top glove in a stack of one or more gloves in a manner which causes the top glove to be expanded open by the air flow without the assistance of any sort of wrist-opening supporting device or the establishment of a sealed vacuum compartment. As a result, the operator may quickly and simply insert a hand into the glove and immediately remove the gloved hand without needing to contact any surface of the glove other than its interior.

The gloves may be arranged in a stack having relatively small tabs on the lower edge of the glove wrist opening which provide for contact and retention on at least one of the next lower glove in the stack and the stack itself. The retention may result from a variety of approaches, such as the presence of an adhesive on the lower face of a connecting tab or by use of glove stacking tabs on the heel of the glove, as long as the approach: (i) permits the top glove on the stack to be inflated by gas flow while the tab or other stacking aid retains the top glove on the stack and helps to keep the next glove down in the stack from opening in response to the air flow; (ii) the topglove's heel tab is readily released from the stack as the operator removes their gloved hand from the machine; and (iii) removal of the top glove and its tab or other stacking aid permits the next glove in the stack to immediately inflate in the air flow so as to be quickly ready for the next operator hand insertion.

Further objects of the invention have been achieve by providing a method for donning gloves including the steps of operating a gas flow generating source to create a gas flow across at least a top glove in a stack of gloves in an unsealed glove inflation chamber, inserting a hand into the top glove which has inflated upon establishing the gas flow past the top glove in the glove inflation chamber, moving the top glove with the hand away from the stack of gloves to separate the top glove from the stack of gloves. The method for donning gloves further may include the step of, after inserting the hand into the top glove, disrupting the gas flow in the glove inflation chamber, and the step of disrupting the gas flow to facilitate removal of the gloved hand by at least one of operating a bypass valve to disrupt flow into an opening of the glove inflation chamber, operating an outlet valve to disrupt flow out of an outlet opening of the glove inflation chamber, and turning off the gas flow generating source by at least one of manual and automatic actuation of a power switch of the gas flow generating source.

Further advantageous refinements and preferred aspects of the invention will be apparent from a consideration of the following description and claims and the accompanying drawing figures.

BRIEF DESCRIPTION OF THE DRAWINGS

The invention will be described in further detail hereinafter with reference to illustrative preferred embodiments shown in the accompanying drawing figures, in which.

DETAILED DESCRIPTION

Figure 1:
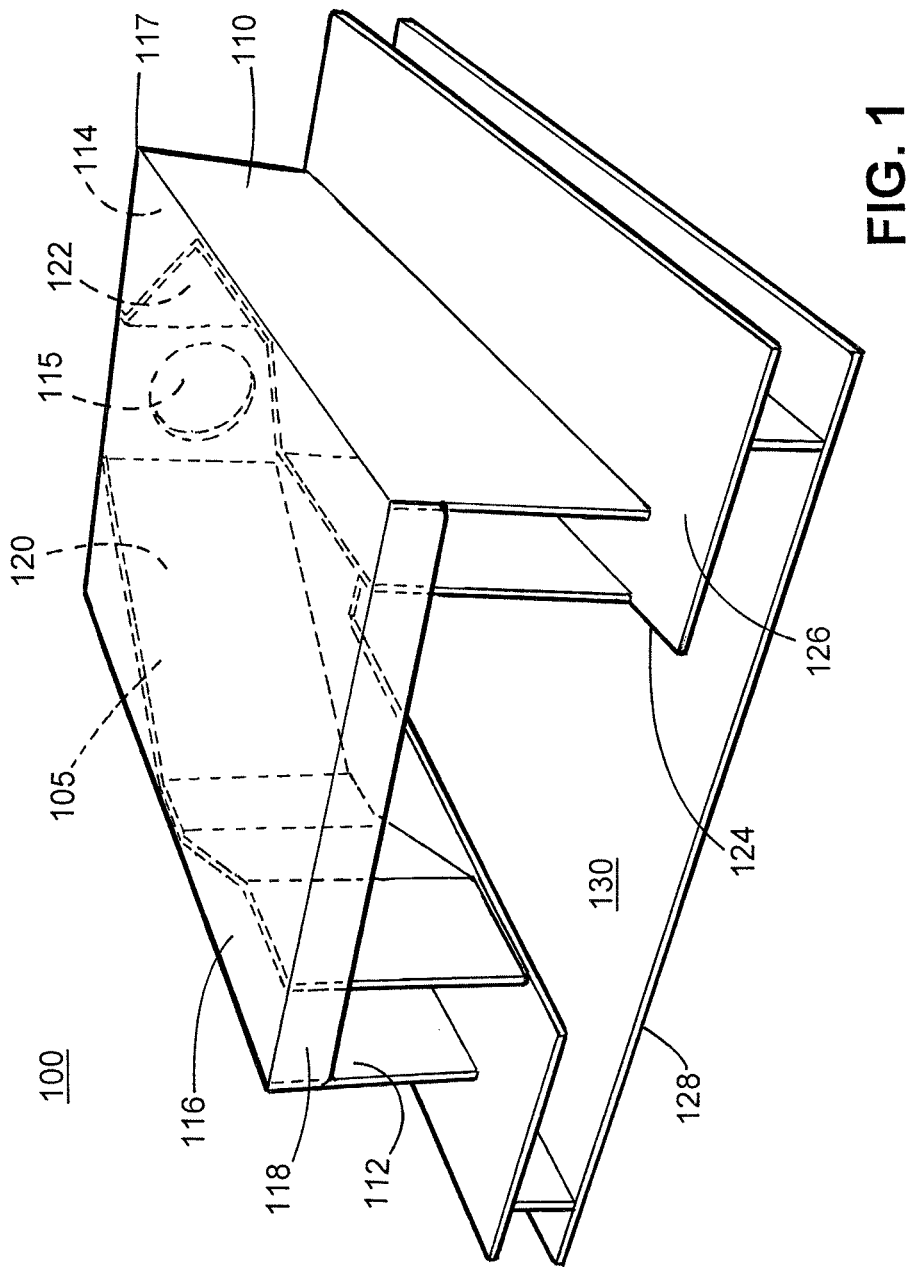
FIG. 1 is a perspective view of an illustrative embodiment of a glove dispensing and applying apparatus according to the invention in which interior components are depicted in broken lines.

FIG. 1 illustrates a view of a glove dispensing apparatus 100 in accordance with an embodiment of the present invention. In this arrangement, a glove inflating chamber 105 is formed within a box-shaped structure having side walls 110, 112, rear wall 114 and a hinged lid 116. The rear wall 114 has a gas outlet opening 115 (here, a round port) through which a gas (in this embodiment, air) is drawn during operation of the glove dispensing apparatus 100, as discussed further below. The hinged lid 116 pivots in the vicinity of the rear wall 114 about axis 117, acting as a valve which alters the gas flow through the glove inflating chamber 105 as the lid 116 is opened and closed. The hinged lid 116 also includes a front panel 118 which helps control air flow during operation of the glove dispensing apparatus 100, as discussed further below. The glove inflating chamber 105 also includes internal air flow control walls 120, 122 which are shaped to generally closely conform to an outer profile of a glove.

In this embodiment, the glove inflating chamber 105 is located about a cutout 124 in the floor plate 126 upon which the box-shaped glove inflating chamber 105 is located. The floor plate is located above a base plate 128, thereby defining a recessed platform area 130 in which a stack of gloves may be placed in preparation for glove donning (stack not illustrated for clarity, see example stack details in FIGS. 5, 6, 6A).

Figure 2:
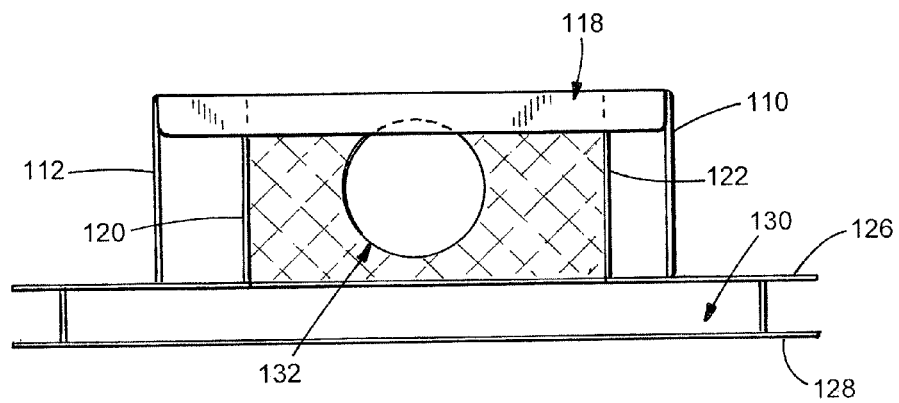
FIG. 2 is a front elevation view of the apparatus of FIG. 1.
Figure 3:
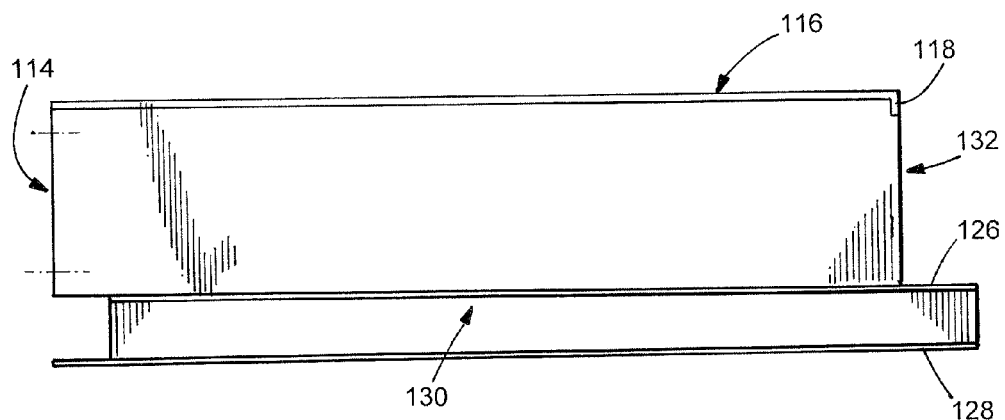
FIG. 3 is a side elevation view of the apparatus of FIGS. 1 and 2.

FIGS. 2 and 3 show front elevation and side elevation views, respectively, of the FIG. 1 embodiment. The FIG. 2 view in particular shows the relatively constrained size of the front opening 132, a feature which enhances air flow about the open end of the top glove in the stack of gloves. The configuration of the front opening 132 also illustrates a feature of the present invention, the lack of reliance on a completely sealed operating environment to ensure adequate inflation of the glove for hand insertion, unlike the case in the patents identified above. This greatly reduces the design complexity and operational issues, as there is no need for installation or other handling of the gloves in order to prepare them for mounting in a sealing fixture, as in prior art glove inflation machines.

Figure 4:
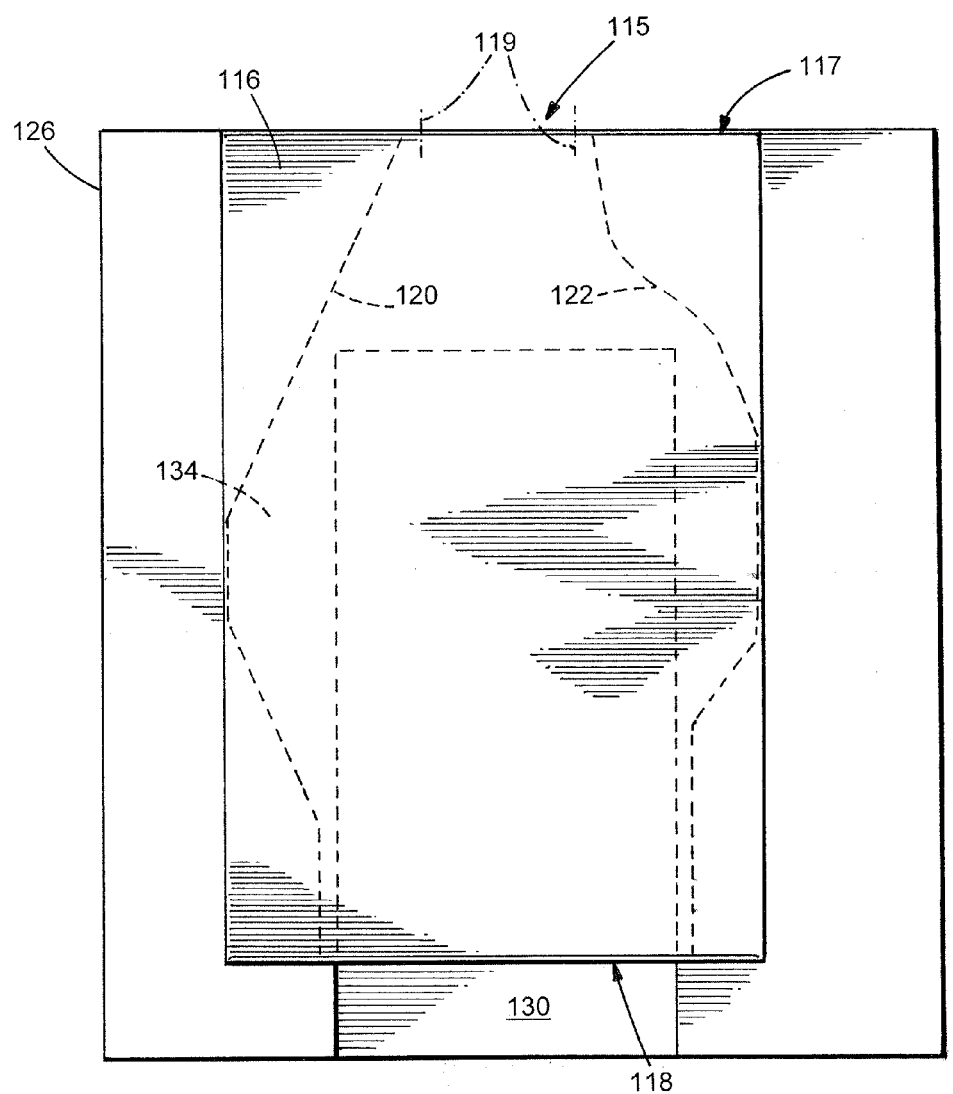
FIG. 4 is a top view of the apparatus of FIGS. 1-3.

FIG. 4 is a top view of the FIG. 1 apparatus, showing the generally glove-shaped region 134 between internal air flow control walls 120, 122 within glove inflation chamber 105. The shape of the generally glove-shaped region 134, corresponding generally to a plan view profile of the stack of gloves, is provided to maintain consistent air flow velocity around the top glove in the stack of gloves to help maintain the inflated glove shape during glove donning.

Figure 5:
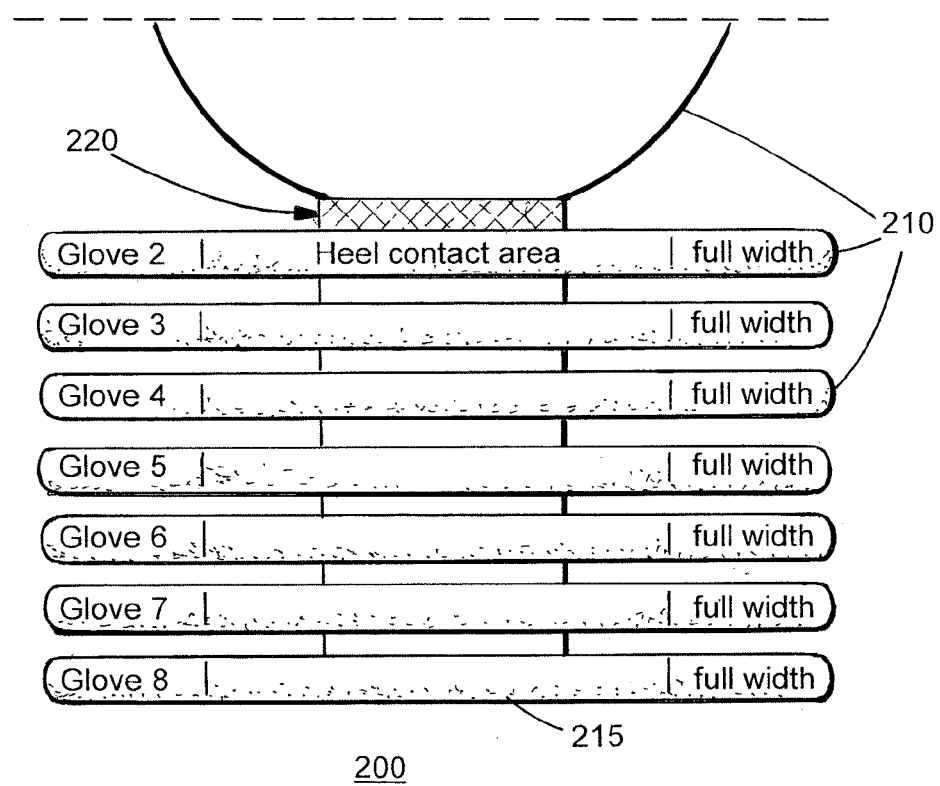
FIG. 5 is an enlarged detail end view of the stacking arrangement of a series of gloves in a glove cartridge adapted for use in the apparatus of the invention.
Figure 6:
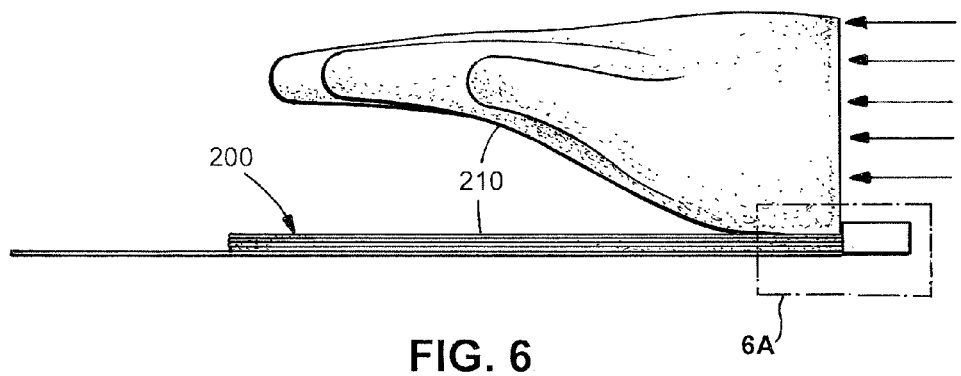
FIG. 6 is a side view of a glove cartridge in the apparatus of the invention with the topmost glove inflated and ready to receive the hand of a user.
Figure 6A:
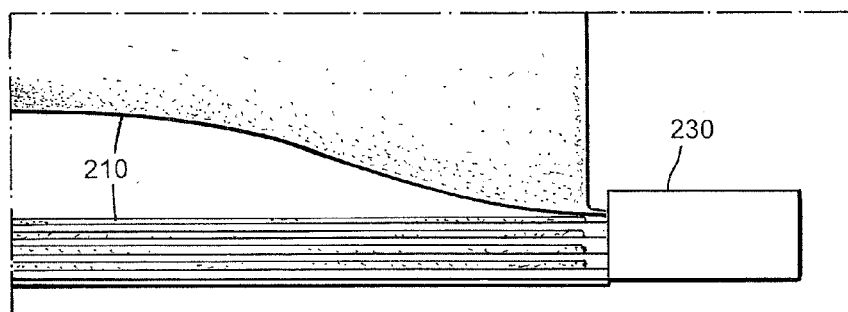
FIG. 6A is an enlarged detail view of a portion of the glove cartridge of FIG. 6 in the area identified by rectangle A showing how the topmost glove prevents inflation of the underlying gloves.

Details of an arrangement of a stack of gloves well suited to use with the FIG. 1 apparatus embodiment of the present invention are shown in FIGS. 5, 6 and 6A. FIG. 5 shows an elevation view of a stack 200 of gloves 210. In this embodiment of the stack of gloves, the gloves 210 are stacked on top of one another. As seen in the FIG. 5 elevation view, the gloves 2-7 in the stack of gloves 200 have a full width which is accommodated in the generally glove-shaped region 134 of the apparatus 100, while the width of the front opening 132 of the glove inflation chamber 105 generally corresponds to the width of the heel of the gloves 215.

In this embodiment of the stack 200, there is no connection between the gloves 210 except for a relatively small glove heel contact area 220 located within the width of the heel of the gloves 215. This heel contact area 220 is located only on a lower portion of the glove heel opening, and is provided to act as an anchor for the top glove. This anchor holds the top glove in the stack in place while the glove is being inflated, yet does not offer significant resistance to separation of the top glove from the stack 200 after the user has inserted a hand into the top glove and pulled the glove out of the apparatus 100. The width of the heel contact area may vary, so long as sufficient contact, is provided to secure the glove to the glove stack until a hand is inserted and the glove is removed, while still allowing the upper surface of the topmost glove to rise enough to allow a hand sufficient room to enter the glove. In a preferred embodiment, the secured portion in the heel contact area 220 may extend along from 10 to 50% of the glove width, and further along from 15 to 35% of the glove width.

A similar heel contact area is provided between each of the gloves in the glove stack 200. One of ordinary skill will recognize that there are many ways to provide such a connection between the heel contact area 220 and either the next lower glove or the rest of the glove stack while still providing for easy removal of the top glove from the stack. For example, the use of a low-adhesion adhesive over a small area would serve these functions, as would use of an easily torn-off tab at the heel of the glove, the use of a thermal bonding process such as thermal fusion, or the use of a series of interlocking molded surface features. This glove stacking approach provides a low-cost approach to glove preparation for inflation, and greater hygiene as the individual gloves do not have to be handled (and thus potentially contaminated by the handler) in order to prepare the gloves for inflation.

In operation, the embodiment illustrated in FIGS. 1-6A functions as follows.

First, a glove stack 200 is placed in the recessed platform area 130, aligned with the generally glove-shaped region 134 and with the glove heel region at the front opening 132 of the glove inflation chamber 105. The lid 116 is lowered to close off the top of the glove inflation chamber 105, and an air flow generating source 119 is turned on, either manually by the operator or automatically, such as when triggered by a switch as the lid 116 is closed or when the presence of an approaching hand is detected by a proximity sensor. The air flow generating source may be any device which creates a sustained air flow through the glove inflation chamber 105, such as a blower with its suction side connected to rear port 115.

Because a high vacuum need not be established in the glove inflation chamber 105, the blower which creates the air flow need not be a high-power vacuum pump, but instead needs only establish a sufficient air flow to accomplish the top glove lifting action described below. This permits the use of a lower power and less costly blower than was often needed in the prior art sealed vacuum-based glove inflation machines.

When the air flow generating source is turned on, a relatively high velocity air flow is established in the glove inflation chamber 105, with the air entering the chamber via constrained front opening 132 and being drawn out of the rear of the chamber via port 115. The relatively high air flow velocities are achieved, despite the relatively low power of the air flow generating source, as a result of the close confirmation of the walls 120, 122 around the sides of the top glove, and with the assistance of lid 116's front panel 118, which reduces the cross-sectional area of the front opening 132 above the glove stack 200.

One of ordinary skill will recognize that in accordance with Bernoulli's law, as the air flow velocity over and around the top glove increases, there is a corresponding drop in the local air pressure around the exposed surfaces of the top glove. One of ordinary skill will also recognize that due to the heel opening of the glove facing the incoming air flow, a pressure difference is created between the interior of the top glove and the exterior of the glove, causing the upper surface of the glove to begin to rise automatically, i.e., without any contact between the operator and the glove exterior, and thereby preserving the hygiene of the glove.

The top glove continues to inflate in the glove inflation chamber 105 until it reaches its fully inflated state as shown in FIG. 6. The top glove remains fully inflated as long as the air flow generating source is operating to maintain the air flow through the chamber and the hinged lid 116 remains closed. As shown in FIG. 6A, the top glove is retained in place on the top of the glove stack 200 by its connection to the next lower glove at the glove heel contact area 220. In the FIG. 6A illustration, the heel contact area 220 of the top glove is connected to the next lower glove (and the remaining gloves in the glove stack 200) by a common tear-off block 230. Because the heel contact area 220 of the topmost glove in the stack covers the heel opening of the next lower glove in the stack, no significant amount of air may enter the next lower glove through its wrist opening. As a result, the next lower glove is constrained from inflating while the top glove is still attached to the stack of gloves 200.

Once the top glove is inflated, the operator need only insert their hand into the standing-open glove, and once fully inserted, simply lift the lid 116 (thereby disrupting the air flow in the closely-conforming glove inflation chamber 105) to allow them to lift their gloved hand out of the chamber. Because the strength of the retention feature between the top glove and the next lower glove in the glove heel contact area 220 is relatively weak (i.e., strong enough to retain the top glove in the face of the relatively small aerodynamic forces created by the air flow through the chamber 105, but weak enough to be easily released as the operator lifts their hand out of the chamber), the operator may very quickly don the topmost glove in the stack 200 and remove their gloved hand from the glove dispensing apparatus 100 very rapidly. This is in contrast to some prior art machines which required significant set-up time and time-consuming multiple-step operations to install the glove into its held-open position and to then extract the gloved hand and prepare the machine for inflation of the next glove.

Once the operator's freshly-gloved hand is removed from the glove dispensing apparatus 100, the operator may turn the air flow generating source off. Alternatively, the operator may lower the hinged lid 116 back down over the glove inflating chamber 105. If the lid 116 is lowered after turning off the air flow generating source, the apparatus will be in a condition where when turned back on, the next lower glove in the glove stack 200 (now the new top glove) will be automatically inflated in response to the re-established air flow through the glove inflating chamber 105.

Alternatively, if the air flow generating source remains turned on, when the lid 116 is lowered back down to again close off the top of the glove inflation chamber 105, the next lower glove in the glove stack 200 (now the new top glove) will immediately begin to inflate as the air flow through the front opening 132 and the glove conforming-shaped portions the glove inflating chamber 105 is begins to be restored. Thus, by a very simple operation which in some embodiments requires at most only a few seconds, the operator may nearly instantly don one or two fresh, untouched hygienic gloves and immediately return to their work tasks.

The foregoing description and examples have been set forth merely to illustrate the invention and are not intended to be limiting. For example, rather than lifting the lid 116 of the glove inflating chamber 105 to disrupt the air flow in the chamber, a closure valve which blocks the flow of gas out of the outlet port 115 may be used to reduce the air flow in the chamber to the point that the air flow will not inflate the top-most glove in the glove stack 200. Similarly, rather than providing an apparatus having a single glove inflation chamber, multiple chambers (such as a left chamber and a right chamber may be provided to permit simultaneous donning of gloves on both hands of an operator. Since modifications of the describe embodiments incorporating the spirit and substance of the invention may occur to persons skilled in the art, the invention should be construed broadly to include all variations within the scope of the appended claims and equivalents thereof.

What is claimed is:

1. A glove dispensing apparatus comprising:
   an enclosed glove inflation chamber having:
      a hand insertion opening at a first end of the chamber, and
      a gas outlet opening at a second end of the chamber;
   a plurality of gloves arranged in a stack in said chamber, each glove having an open end adjacent to said hand insertion opening and a closed end adjacent to the gas outlet opening, and each glove being secured to the stack of gloves along a portion of one side of the open end;
   a gas flow generating source which communicates with said outlet opening for drawing a gas flow through the hand insertion opening, the dispensing chamber and through said gas outlet opening;
   wherein said enclosed glove inflation chamber is arranged such that the gas flow generated by the gas flow generating source creates a reduced pressure in the enclosed glove inflation chamber near an outer surface of a topmost glove in said stack so as to cause the topmost glove to inflate to permit a user to insert a hand into the inflated glove.

2. The apparatus according to claim 1, further comprising:
   a bypass valve for selectively admitting gas to said dispensing chamber, said bypass valve being arranged such that when the bypass valve is actuated the gas flow through the hand insertion opening is diminished so that the gas flow is insufficient to inflate the topmost glove in said stack.

3. The apparatus according to claim 1, further comprising:
an outlet valve for selectively blocking said gas outlet, said outlet valve being arranged such that when the outlet valve is actuated the gas flow through the chamber outlet opening is diminished so that the gas flow is insufficient to inflate the topmost glove in said stack.

4. The apparatus according to claim 1, wherein said source of reduced gas pressure is a vacuum cleaner.

5. The apparatus according to claim 1, wherein each glove has a heel contact area along said portion of said one side of said open end, and the heel contact areas of the gloves are joined together to form said glove stack.

6. The apparatus according to claim 5, wherein the heel contact area is a tab, and the tabs of the gloves in the stack are joined together.

7. The apparatus according to claim 6, wherein said tabs are joined by adhesive bonding.

8. The apparatus according to claim 6, wherein said tabs are joined by thermofusion.

9. The apparatus according to claim 6, wherein each said tab is joined to the respective glove via a weakened section which allows the glove to be easily torn from the stack.

10. The apparatus according to claim 9, wherein said weakened section comprises a perforated tear line.

11. The apparatus according to claim 1, wherein the secured portion of the one side of the open end of each glove extends along from 10 to 50% of the glove width.

12. An apparatus according to claim 1, wherein the secured portion of the one side of the open end of each glove extends along from 15 to 35% of the glove width.

13. The apparatus according to claim 1, wherein the closed end of each glove is divided into a plurality of individual finger sections.

14. The apparatus according to claim 1, wherein the glove inflation chamber includes left and right glove inflation chambers disposed proximate each other in an arrangement which permits simultaneous insertion of left and right hands into left and right gloves in the respective left and right chambers.

15. The apparatus according to claim 2, wherein said bypass valve comprises a pivotable wall section of said chamber.

16. The apparatus according to claim 1, further comprising:
a proximity sensor arranged to detect a hand approaching said hand insertion opening, said proximity sensor being operatively connected to the gas flow generating source to turn on the gas flow generating source as the hand approaches the hand insertion opening.

17. The apparatus according to claim 1, wherein said glove inflation chamber has side walls contoured to approximately follow a plan view profile of the stack of gloves.

18. A method for donning gloves, comprising the steps of:
initiating operation of a gas flow generating source to create a gas flow across at least a top glove in a stack of unopened gloves in an unsealed glove inflation chamber;
inserting a hand into the top glove which has inflated upon establishing the gas flow past the top glove in the glove inflation chamber; and
moving the top glove with the hand away from the stack of gloves to separate the top glove from the stack of gloves.

19. The method for donning gloves according to claim 18, further comprising the steps of:
after inserting the hand into the top glove, disrupting the gas flow in the glove inflation chamber.

20. The method for donning gloves according to claim 19, wherein
the gas flow is disrupted by at least one of:
operating a bypass valve to disrupt flow into an opening of the glove inflation chamber,
operating an outlet valve to disrupt flow out of an outlet opening of the glove inflation chamber, and
turning off the gas flow generating source by at least one of manual and automatic actuation of a power switch of the gas flow generating source.

\* \* \* \* \*